(12) United States Patent
Weaver, II et al.

(10) Patent No.: US 7,364,558 B2
(45) Date of Patent: Apr. 29, 2008

(54) BACK SUPPORT PANEL WITH CONVEX SURFACES FOR MUSCLE SUPPORT

(75) Inventors: Edward L. Weaver, II, Milford, OH (US); Sherry A. Hinds, Goshen, OH (US)

(73) Assignee: Beiersdorf, Inc., Wilton, CT (US)

( * ) Notice: Subject to any disclaimer, the term of this patent is extended or adjusted under 35 U.S.C. 154(b) by 454 days.

(21) Appl. No.: 10/274,351

(22) Filed: Oct. 18, 2002

(65) Prior Publication Data

US 2004/0077981 A1    Apr. 22, 2004

(51) Int. Cl.
*A61F 5/28* (2006.01)
*A61F 5/02* (2006.01)

(52) U.S. Cl. ..................... 602/19; 297/230.1

(58) Field of Classification Search ............... 602/19, 602/14, 5, 1; 2/311, 318, 319, 338; 297/230.1–230.13, 297/452.29–452.37; 450/155
See application file for complete search history.

(56) References Cited

U.S. PATENT DOCUMENTS

| | | | |
|---|---|---|---|
| 2,726,714 A | | 12/1955 | McAndrews |
| 2,733,712 A | * | 2/1956 | Wuesthoff .................. 602/19 |
| 2,858,827 A | * | 11/1958 | Vilpou ........................ 602/19 |
| 3,052,236 A | | 9/1962 | Schrieber |
| 3,171,409 A | | 3/1965 | Cetrone |
| 3,400,710 A | | 9/1968 | Goldstein |
| 3,434,469 A | | 3/1969 | Swift |
| 3,713,437 A | | 1/1973 | Weidmer |
| 3,717,143 A | * | 2/1973 | Johnson ........................ 602/19 |
| 4,135,503 A | * | 1/1979 | Romano ....................... 602/13 |
| 4,159,020 A | * | 6/1979 | von Soiron et al. ............ 601/1 |
| 4,178,923 A | * | 12/1979 | Curlee .......................... 602/13 |
| 4,243,028 A | | 1/1981 | Puyana |
| 4,245,628 A | | 1/1981 | Eichler |
| 4,475,543 A | | 10/1984 | Brooks et al. |
| 4,552,135 A | | 11/1985 | Racz et al. |
| 4,572,167 A | * | 2/1986 | Brunswick .................. 602/19 |
| 4,597,386 A | * | 7/1986 | Goldstein ..................... 602/19 |
| 4,616,639 A | | 10/1986 | Huber |

(Continued)

FOREIGN PATENT DOCUMENTS

DE    101 03 545 A1    8/2002

(Continued)

*Primary Examiner*—Patricia Bianco
*Assistant Examiner*—Huong Q. Pham
(74) *Attorney, Agent, or Firm*—Alston & Bird LLP

(57) ABSTRACT

A back brace for supporting a lower back region of a wearer that includes a strapping system that supports a lumbar support panel at the lower back region of the wearer. The lumbar support panel includes an inner surface adjacent to the wearer's back defining a pair of raised support regions that have convexly curved outer surfaces and medial edges spaced apart from each other. Advantageously, the spacing between the medial edges provides clearance for the lower spine of the wearer to prevent discomfort. In addition, the convexly curved medial edges improve the support panel's fit to the contours of the wearer's back and avoid pressure points on the wearer's erector spinae musculature through a relatively even pressure distribution on the musculature. The lumbar support panel also may include a plurality of ventilation holes and may be constructed of "skin-friendly" materials that wick moisture away and allow air in for additional comfort.

24 Claims, 7 Drawing Sheets

U.S. PATENT DOCUMENTS

| | | |
|---|---|---|
| 4,627,109 A | 12/1986 | Carabelli et al. |
| 4,703,750 A | 11/1987 | Sebastian et al. |
| 4,745,911 A | 5/1988 | Bender |
| 4,768,499 A | 9/1988 | Kemp |
| 4,794,916 A * | 1/1989 | Porterfield et al. ............ 602/19 |
| 4,796,315 A | 1/1989 | Crew |
| 4,833,730 A | 5/1989 | Nelson |
| 4,836,194 A | 6/1989 | Sebastian et al. |
| 4,907,576 A * | 3/1990 | Curlee ......................... 602/19 |
| 4,997,438 A | 3/1991 | Nipper et al. |
| 5,040,524 A | 8/1991 | Votel et al. |
| 5,046,488 A | 9/1991 | Schiek, Sr. |
| 5,093,931 A | 3/1992 | LaBerge et al. |
| 5,147,261 A | 9/1992 | Smith et al. |
| 5,178,163 A | 1/1993 | Yewer, Jr. |
| 5,257,419 A | 11/1993 | Alexander |
| 5,316,022 A | 5/1994 | Schiek, Sr. |
| 5,399,150 A * | 3/1995 | Saunders ..................... 602/19 |
| 5,429,587 A | 7/1995 | Gates |
| 5,484,395 A * | 1/1996 | DeRoche ..................... 602/19 |
| 5,533,961 A * | 7/1996 | Iwata .......................... 602/19 |
| 5,551,085 A * | 9/1996 | Leighton ......................... 2/44 |
| 5,651,763 A * | 7/1997 | Gates .......................... 602/19 |
| 5,776,087 A | 7/1998 | Nelson et al. |
| 5,785,671 A | 7/1998 | Striano |
| 5,830,167 A * | 11/1998 | Jung ........................... 602/19 |
| 5,833,638 A | 11/1998 | Nelson |
| 5,915,543 A | 6/1999 | Julin |
| 5,984,885 A | 11/1999 | Gaylord, Jr. et al. |
| 6,080,121 A | 6/2000 | Madow et al. |
| 6,102,879 A | 8/2000 | Christensen et al. |
| 6,137,675 A | 10/2000 | Perkins |
| 6,190,343 B1 * | 2/2001 | Heinz et al. .................. 602/19 |
| 6,319,217 B1 * | 11/2001 | Darcey ....................... 602/19 |
| 6,336,908 B1 * | 1/2002 | Slautterback ................ 602/19 |
| 6,419,652 B1 * | 7/2002 | Slautterback ................ 602/19 |
| 2001/0020144 A1 | 9/2001 | Heinz et al. |
| 2002/0068890 A1 | 6/2002 | Schwenn et al. |

FOREIGN PATENT DOCUMENTS

| | | |
|---|---|---|
| EP | 0 636 325 A2 | 2/1995 |
| WO | WO 02/058602 A1 | 8/2002 |

* cited by examiner

BACK SUPPORT PANEL WITH CONVEX SURFACES FOR MUSCLE SUPPORT

BACKGROUND OF THE INVENTION

1. Field of the Invention

The present invention is directed to orthopedic back support braces, and more particularly to back braces for providing localized support for musculature of the lower lumbar spine of a wearer of the back brace.

2. Description of Related Art

Lower back pain is a very common occurrence that afflicts many people and can be acute, such as when associated with a single traumatic event, or chronic, such as from the rigors of manual labor associated with certain types of employment. Despite the pervasiveness of lower back pain, most surgical options for treating lower back injuries are invasive and are therefore typically reserved for the worst back injuries. Short of such surgery, most treatments for lower back injuries comprise either pain management with the use of over-the-counter or prescription drugs, or stabilization the lower back through the use of an orthopedic back brace. Advantageously, orthopedic back braces provide additional support to the lower back during lifting, bending and other activities. In addition, the back brace supplements the proprioception of the wearer by reminding the wearer of the limitations caused by the injury, thereby promoting recovery and avoiding further injury.

U.S. Pat. No. 5,551,085 to Leighton ("Leighton") discloses a lower lumbar support 10 including a support belt 12 constructed of an elastic material, a pair of pressure pads 14, 16 positioned at the lower back of a wearer and a pressure strap 18 attached to the support belt and extending over the pressure pads, as shown in FIGS. 1, 2 and 8 of Leighton. As shown by FIG. 9 of Leighton, the pads include protrusions 5, 6 that extend from the belt and contact the wearer's lower back muscles on opposite sides of the spine. The pads are either rectangular, as shown in FIG. 1, or semi-elliptical as shown in FIG. 2, with the pads in each configuration having opposing straight medial edges providing clearance for the spine. During use, the support belt is tightened about the wearer's waist and the pressure exerted by the pads is adjusted by adjusting the tightness of the overlapping pressure strap. Despite allowing for adjustability of the pressure exerted by the pads, improvements are still needed that balance both the support provided by the back brace with the comfort of wearing the brace.

Therefore, it would be advantageous to have a back brace that provides firm support for a wearer's lumbar spine. In addition, it would be advantageous if the back brace included support features that were comfortable to wear without sacrificing the firm support, thereby enhancing the overall effectiveness of the back brace by increasing its frequency of use.

BRIEF SUMMARY OF THE INVENTION

The present invention overcomes the above problems and achieves other advantages by providing a back brace for supporting a lower back region of a wearer. The back brace includes a strapping system that supports a lumbar support panel at the lower back region of the wearer. The lumbar support panel includes an inner surface adjacent to the wearer's back and defining a pair of raised support regions that have convexly curved outer surfaces and medial edges spaced apart from each other. Advantageously, the spacing between the medial edges provides clearance for the lower spine of the wearer to prevent discomfort. In addition, the convexly curved medial edges improve the support panel's fit to the contours of the wearer's back and avoid pressure points on the wearer's erector spinae musculature through a relatively even pressure distribution on the musculature. The lumbar support panel also may include a plurality of ventilation holes and may be constructed of "skin-friendly" materials that wick moisture away and allow air in for additional comfort.

A back brace of one embodiment of the present invention includes a strapping system for supporting a lumbar support panel. The strapping system extends at least partially around the waist of the wearer. Connected to the strapping system, and supported by the strapping system at a lower back region of the wearer, is the lumbar support panel. The lumbar support panel includes an inner surface adjacent to the wearer's back and defining a pair of raised portions wherein each of the raised portions has a convexly curved medial edge. The curved medial edges are spaced apart a distance sufficient to provide clearance for the wearer's lower spine and to contact the wearer's erector spinae musculature with a comfortable, relatively even pressure distribution.

In one aspect, the strapping system may include a pair of main straps each having a free end. At least one of the free ends has a connector attached to it, wherein the connector is configured to connect the free ends together. Connection of the free ends together allows the main straps to be secured around the waist of the wearer. Each of the main straps may also include fixed end attached to the support panel wherein the main straps extend outwards from the fixed ends to the free ends.

In addition to the main straps, the strapping system may further include a pair of outer straps each extending over an outside surface of a respective one of the main straps. Each of the outer straps includes a free end with a connector configured to attach to an outer surface of the respective one of the main straps. For instance, the connector may be a hook material patch for connection to a hook material surface on the outside of the main straps.

The lumbar support panel may include a pair of lateral edges to which the fixed ends of the main straps are attached. Preferably, the lateral edges are angled inwards towards each other at their top ends allowing the lower edge of the main straps to extend at an angle over the wearer's hips, or iliac crests for improved comfort.

In another aspect, the inner surface includes a base surface from which the raised portions extend outwards wherein the base surface extends at least between the convexly curved medial edges. Each of the raised portions may also include a straight lateral edge that extends between the ends of the curved medial edge to form a semi-circular shape.

Optionally, the base surface my define a plurality of air holes that extend through the lumbar support panel for improved ventilation. The air holes may be positioned between the convexly curved medial edges of the raised portions, or may be separated into different groups. For instance, the air holes may be in two groups, one positioned above a shortest distance between the convexly curved medial edges and the other positioned below the shortest distance.

In still another aspect, the raised portions are partially bounded by the convexly curved medial edges and extend outwards from the convexly curved medial edges to form a pair of smoothly curving convex surfaces.

Among other advantages, the lumbar support panel provides comfortable support for the wearer's lower back, in particular through the curved, convex shape of the raised portions on its inner surface that fit the wearer's lordotic curve and avoid forming pressure points on the lower back musculature, especially along their medial edges. Further, the spacing between the raised portions provides clearance for the spinous processes allowing support to be applied to the back musculature. The main and outer straps allow for adjustment of the tension in the back brace and the amount of support provided by the panel. Overall, the strapping system is constructed of relatively thin, breathable and/or moisture wicking fabrics that are comfortable to wear even under clothing, immediately adjacent to the skin. Breathability is further increased by the materials selected for the support panel and the ventilation holes extending through the panel. As another advantage, the angle of the lateral edges of the lumbar support panel angle the main straps upwards to extend comfortably over the hips of the wearer while maintaining the position of the support panel.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
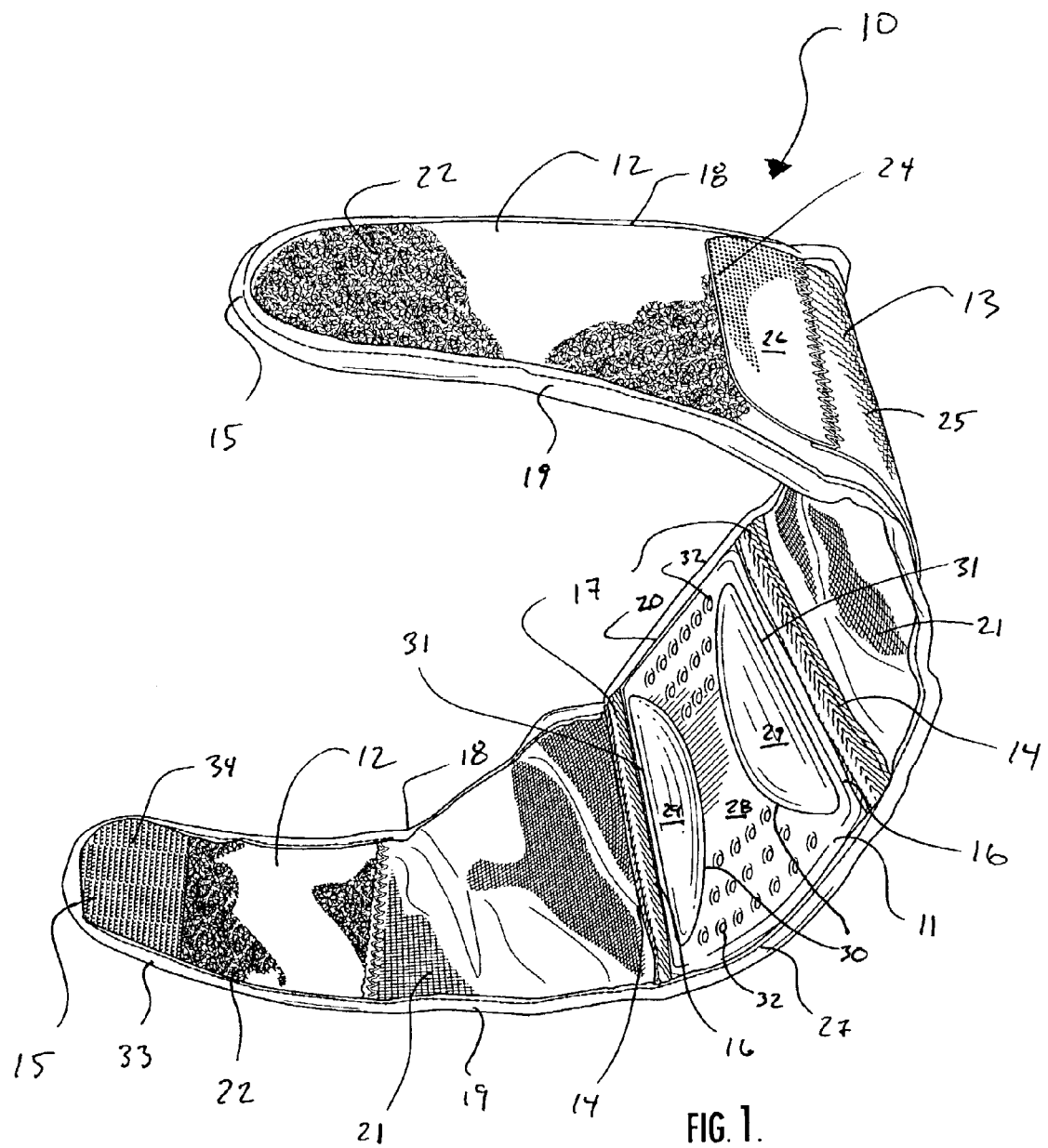
FIG. 1 is a perspective view of a back brace of one embodiment of the present invention.
Figure 2:
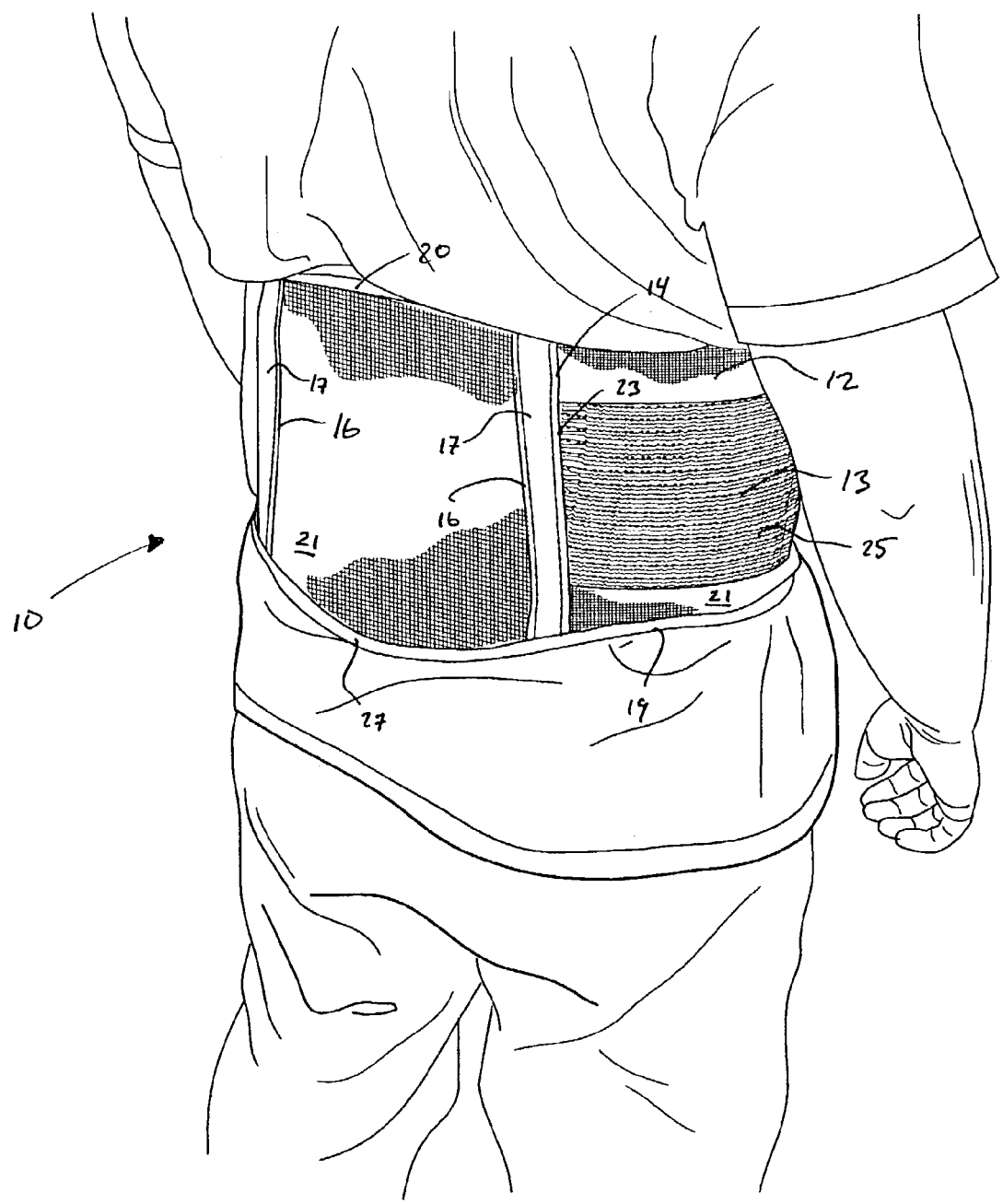
FIG. 2 is a rear, perspective view of the back brace of FIG. 1 secured around the waist of a wearer.
Figure 3:
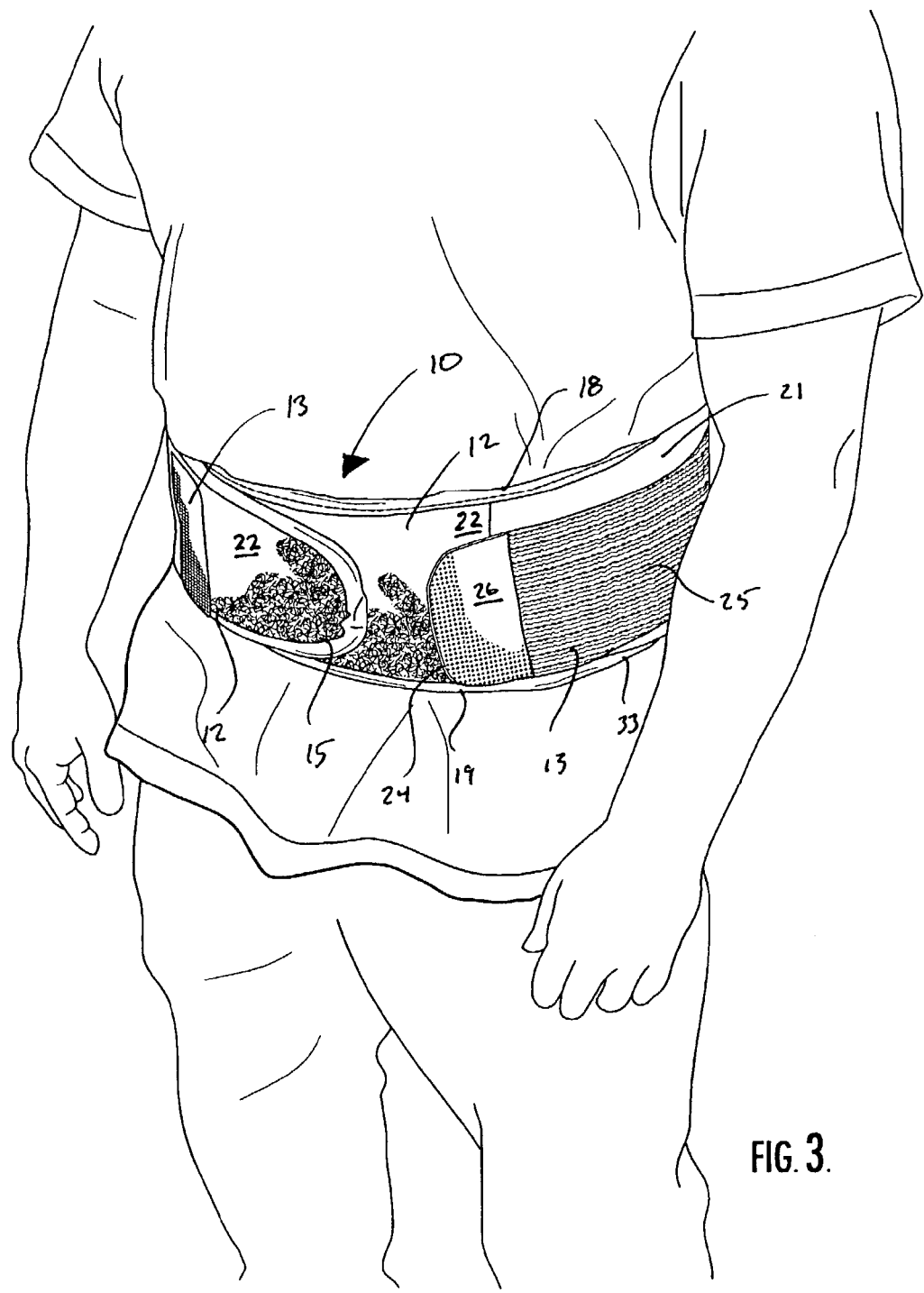
FIG. 3 is a front, perspective view of the back brace of FIG. 1 secured around the waist of the wearer.
Figure 4:
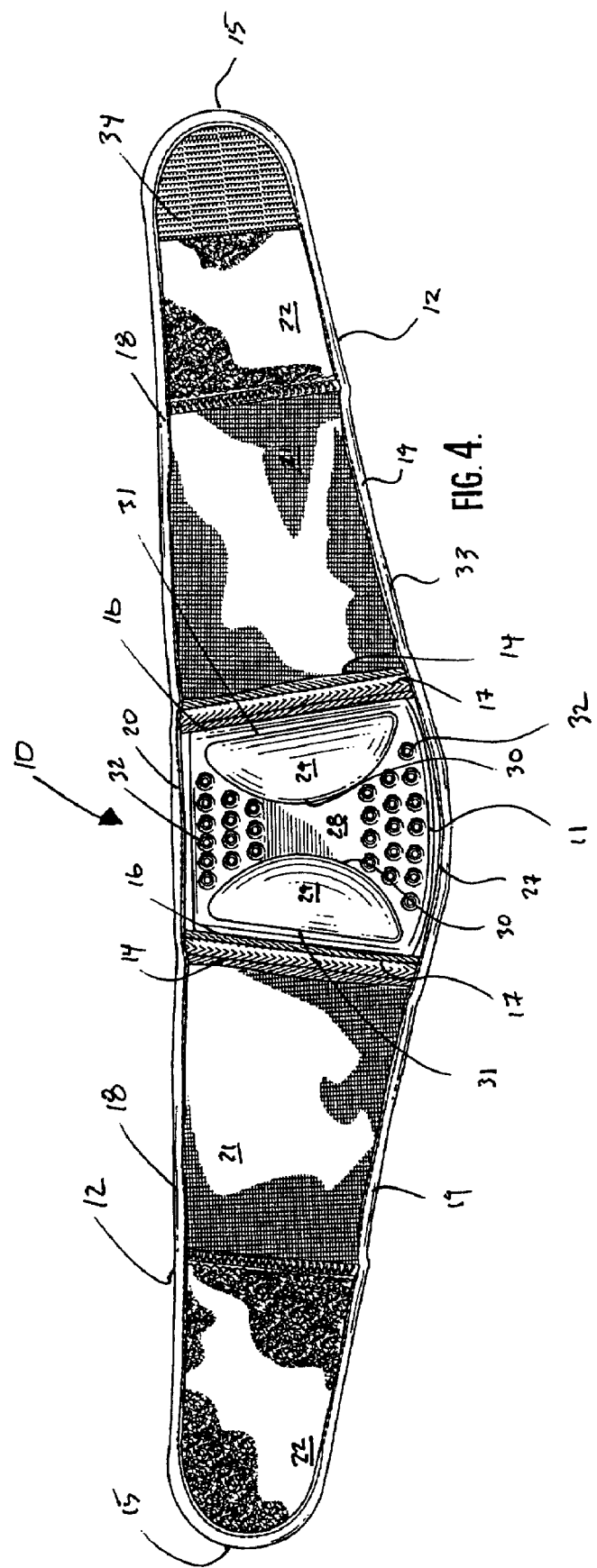
FIG. 4 is a plan view of the back brace of FIG. 1 laid flat and showing its inner surface for positioning adjacent to the wearer's back, including a pair of raised portions defined on a back support panel.
Figure 5:
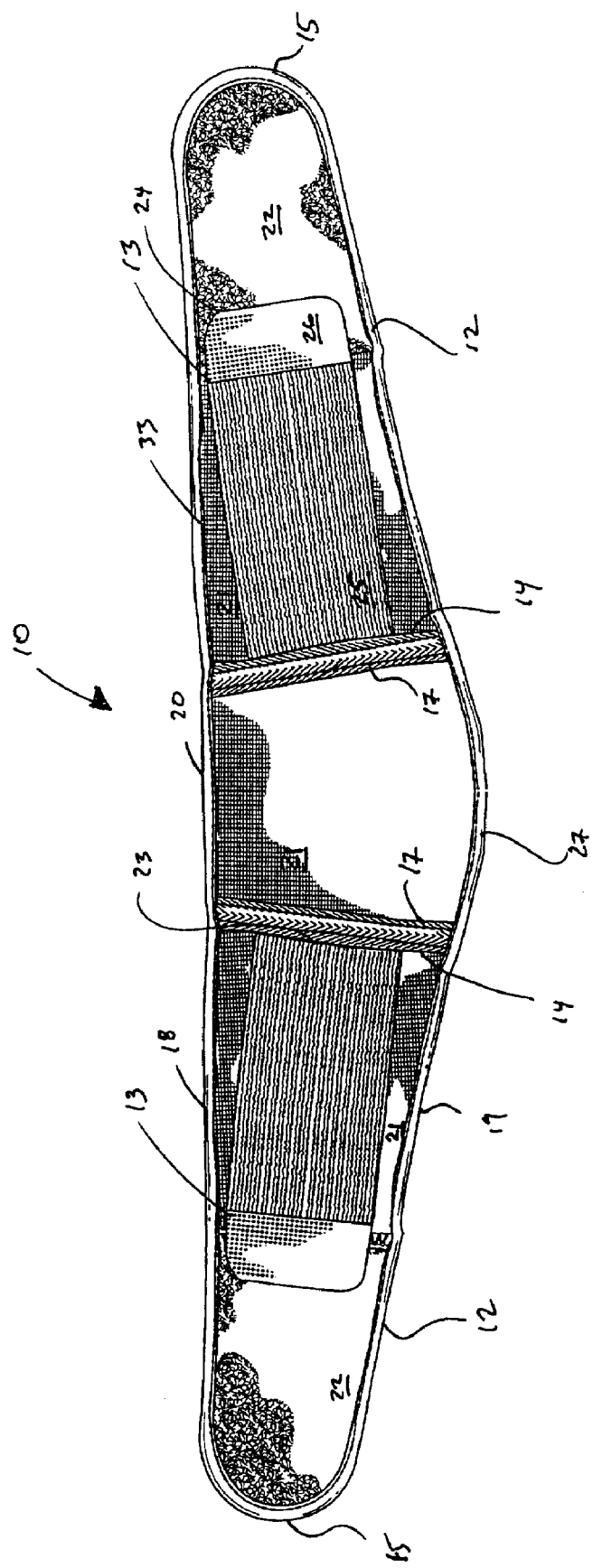
FIG. 5 is a plan view of the back brace of FIG. 1 laid flat and showing its outer surface, including a pair of outer straps overlying a pair of main straps for supporting the back support panel.

A back brace 10 of one embodiment of the present invention includes a lumbar support panel 11 supported by a strapping system that includes a pair of main straps 12 and a pair of outer straps 13, as shown in FIGS. 1, 4 and 5. Generally, the straps 12, 13 extend around the waist of a wearer and support the lumbar support panel 11 at a position over the lower lumbar area of the wearer, as shown in FIGS. 2 and 3.

The main straps 12 each have a fixed end 14 and a free end 15, as best shown in FIGS. 4 and 5. The fixed end 14 of each of the main straps 12 is attached to one of a pair of respective lateral edges 16 of the lumbar support panel 11. Each of the main straps 12 also includes an upper edge 18 and a lower edge 19 extending outwards from the fixed end 14 to the free end 15. The upper edge 18 extends outwards in a straight line, collinear with a top edge 20 of the lumbar support panel 11. The lower edge 19 extends outwards at an angle, generally converging towards the upper edge 18, at about a right angle with respect to the adjacent one of the lateral edges 16 of the lumbar support panel 11 which are themselves angled inwards toward each other at their top ends. The upwards angle of the lower edge 19 results in tapering of the height of the main straps 12 as they extend outwards from the lumbar support panel 11 and end in the free end 15 which has a rounded edge.

Beyond the general geometry of the main straps 12, the main straps are each constructed of two panels of materials corresponding to the fixed end 14 and the free end 15, as shown in FIG. 4. Each fixed end 14 is formed of an end portion of a single, elastic mesh material panel 21 that extends continuously from the fixed end of one of the main straps, over the back of the lumbar support panel 11, to the fixed end of the other one of the main straps. The material panel 21 is preferably constructed of various types of elastic materials and knitting configurations that provide a similar phase, or force required to stretch to a specified elongation. For example, POWERNET stretch elastic material nos. 8686, 5466 or 5452 supplied by CMI Industries, Inc., New York, N.Y. or SPACER stretch elastic fabric no. MSHR711 supplied by Gehering Textiles/Militex, Inc., Garden City, NY may be used for the material panel 21.

Preferably, the mesh material of the fixed end 14 is stitched to the respective one of the lateral edges 16 of the lumbar support panel 11 at a location where the lateral edges and the mesh material initially overlap. It should be noted that although stitching is used to secure most of the materials together in construction of the back brace 10, other attachment types may also be employed such as glues or fasteners.

The seams (not shown) formed by attachment of the mesh material of the fixed end 14 of each of the straps 12 to the lateral edges 16 are preferably covered by four strips, two on an outer side and two on an inner side of the brace 10, of vertically oriented banding material 17 for the comfort of the wearer and improved security. In particular, each strip of vertical banding 17 has two parallel lines of vertical stitching, one line passing through the banding and the mesh material 21 and the other line passing through the mesh material and the support panel 11. The stitching may further extend through the corresponding strip of banding on the opposite side of the back brace 10 for complete front and back coverage of the seam.

Each free end 15 is constructed of a panel of laminate material 22 that has multiple plies, including a soft, moisture-wicking material as its inner, skin-adjacent ply and an outer ply. The laminate material may also include a foam core sandwiched between the skin-adjacent ply and the outer ply. Preferable materials for the outer ply, core ply and inner ply are VELCRO laminates of 3610-0698 UBL, up to 0.125 inch G45L and ORTHOWICK, respectively, or ORTHOWICK, up to 0.125 inch G45L (a urethane foam), 3610-0698 UBL with zero stretch, respectively. Advantageously, the ORTHOWICK or tricot inner ply of the laminate is worn against the skin and has a low skin irritant, soft feel and moisture-wicking properties while the outer ply allows attachment of hook type fasteners, as will be described in more detail below. The laminate material panel 22 is attached to the adjacent edge of the elastic mesh panel 21 via a vertical line of stitching. One of the free ends of the main straps 12 includes a hook-type fastener material panel 34 disposed on its inner surface to allow attachment of the free end to the other one of the free ends.

Each of the pair of outer straps 13 also has a fixed end 23 and a free end 24, as shown in FIG. 5. The outer straps attach at the fixed end 23 to the lumbar support panel 11 and extend outwards therefrom over an outside surface of the main straps 12. Each of the outer straps includes two material panels, an elastic panel 25 which defines the fixed end 23, and a hook material panel 26 that defines the free end 24. The hook material panel 26 is illustrated as having a rectangular shape with rounded edges, but may have a range of other geometric shapes, such as a trapezoid that would minimize contact surface area to avoid skin contact and minimize irritation, or to reduce pull forces required to loosen the strap.

The elastic panel 25 has an elongate, rectangular shape and is formed of an elastic material with a lower elasticity and porosity than the elastic mesh panel 21 material of the main straps 12 for improved resilience and strength. The elastic panel is stitched at the fixed end 23 to the respective one of the lateral edges 16 of the lumbar support panel 11 and to the underlying elastic mesh panel 21. The opposite end of the elastic panel is stitched to the hook material panel 26. The outer strap stretch material panel 25 is preferably a nylon monofilament (vertical)/polyester(horizontal), knit construction having a phase similar to PN #ORTHO3, supplied by George C. Moore Co., Greensboro, N.C.

It should be noted that although the strapping system of the illustrated embodiment, including the main and outer straps 12 and 13, is preferred, the strapping system may include more, or fewer straps, such as a single strap that completely encircles the wearer's waist. The design of the strapping system depends upon factors such as the desired amount of pressure exerted on the back, the need for adjusting the pressure and the desired wearing position. For instance, the strapping may be thinner to be worn under clothes for sports activities, or may be thicker for firmer support outside the clothing for use as a lifting belt. In addition, the materials used in the construction of the strapping system may also be varied to achieve the same objective of positioning and tensioning the lumbar support panel 11 at the lumbar region of the wearer's back.

Figure 6:
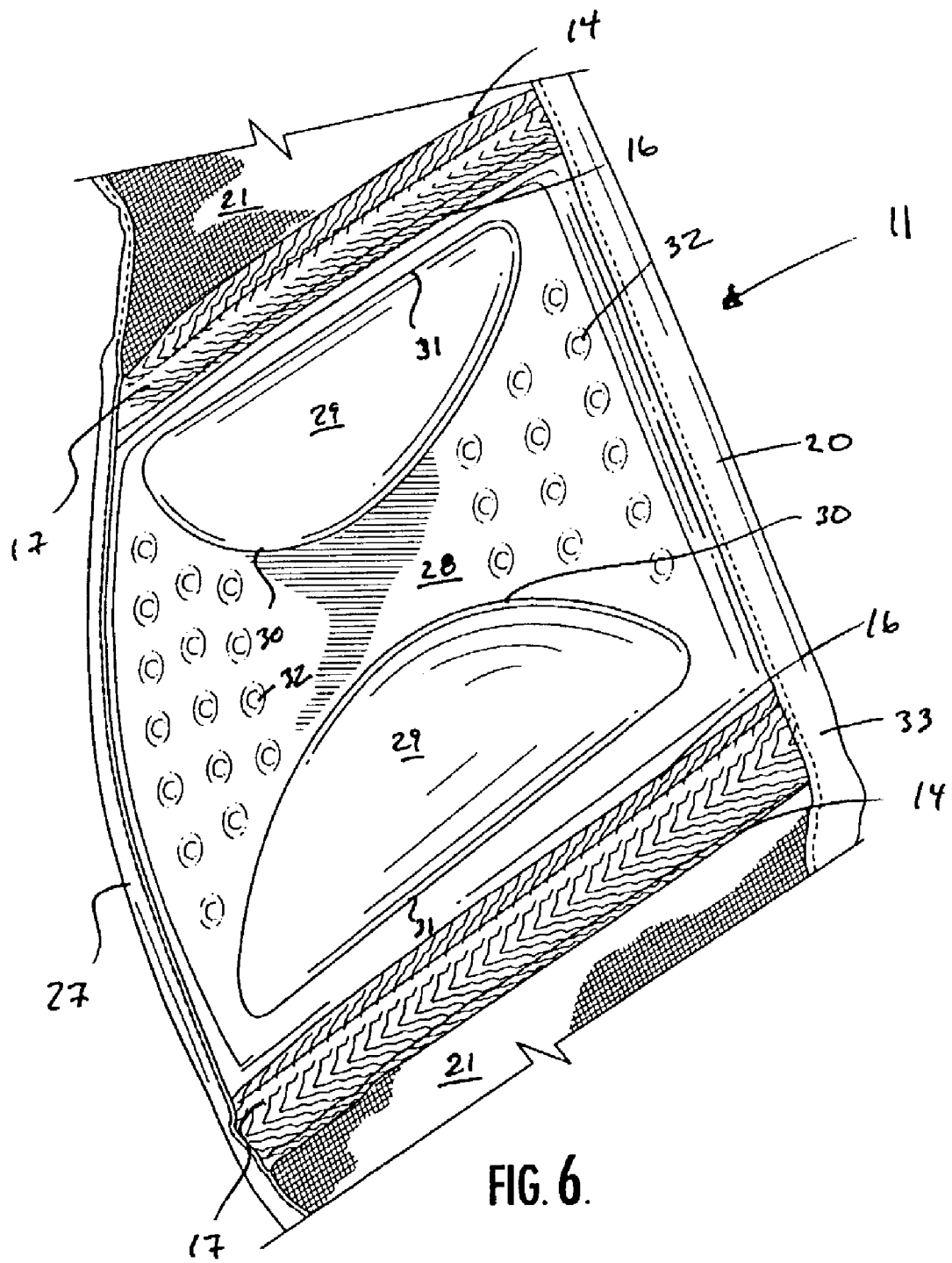
FIG. 6 is an enlarged perspective view of the back support panel shown in FIGS. 1 and 4.

As described above, and as shown in FIG. 6, the lumbar support panel 11 includes a straight top edge 20 and a pair of lateral edges 16. Opposite the top edge 20, which extends between top ends of the lateral edges 16, is a curved bottom edge 11, which extends between the bottom ends of the lateral edges. The lateral edges 16 of the support panel 11 are angled inwards as they extend upwards, slightly converging at their tops to allow the lower edge 19 of the main straps 12 to extend upwards at an angle to pass over the iliac crests of the wearer. In addition, the bottom edge 11 has a curvature that allows it to extend smoothly along the line of each lower edge 19. Together, the top, lateral and bottom edges form an outer peripheral edge of the lumbar support panel 11.

Generally, the lumbar support panel 11 includes an outer face and an inner surface adjacent to the wearer's back that defines a base surface 28 and a pair of raised portions 29. The raised portions each include a convexly curved medial edge wherein the convexly curved medial edges 30 are spaced apart from each other a distance sufficient to accommodate the width of the spinous processes of the wearer. Preferably, the distance is about 1½ to 2 inches to accommodate the width of the lower lumbar spine of an average range of persons. In addition, the centroids of the raised portions 29 are about 3½ to 4½ inches from each other.

The base surface 28 is generally a level surface with the exception of a rounded taper along its peripheral edge promoting the application of banding and connection of the straps 12, 13. The base surface 28 extends around the raised portions 29, and between the convex medial edges 30 of the raised portions. In addition to the convex medial edges 30, each of the raised portions 29 includes a straight lateral edge. Each of the straight lateral edges 31 extends between the top and bottom ends of its respective one of the medial edges 30. In this manner, the raised portions 29 of the illustrated embodiment each have a crescent, or semi-circular, shape that is bounded by the medial and lateral edges 30, 31. The raised portions 29 extend outwards from the base surface 28, peaking at approximately their centroids, to form a pair of smoothly curving convex surfaces. Generally, the raised portions 29 have a height with respect to the base surface of about ⅜ to ⅝ of an inch, and more preferably, about ½ of an inch. The lateral edges 31 are about 5½ inches long and the minimum distance between the curved medial edges 30 and their respective ones of the lateral edges is about 2¼ inches, so as to fit a fairly broad range of wearers.

Generally, the curvature of the convex medial edges 30 and the convex surfaces of the raised portions 29 increase wearer comfort by fitting the natural lordotic curve of the lower back and reducing pressure points on the erector spinae and lower back musculature of the wearer. In addition, the spacing between the medial edges 30 and the height of the raised portions provides clearance for the lower spine, i.e., the spinous processes, of the wearer for further comfort and effectiveness. The shape of each of the curved medial edges 30 of the illustrated embodiment is that of a partial arc of a circle. However, the curved medial edges and raised portions could also have other curved shapes, such as a portion of an ellipse or several arc portions, as long as the shape is generally convex to fit the curve of the lower back and smooth enough to avoid pressure points. Further, the various measurements listed above, and later herein, are for a broad range of people of average size. Therefore, the measurements can be customized for larger or smaller persons, or people with very unique needs such as persons with physical challenges, due to such things as traumatic injury or birth defect, and still achieve the objective of the present invention. Of course customization is somewhat less preferred as the back brace would lose some of the advantages of mass marketability.

Optionally, a plurality of ventilation holes 32 may be defined by the lumbar support panel 11 that extend completely through the lumbar support panel from the inner surface to the outer surface. In the illustrated embodiment, the ventilation holes are defined in two groups, each having three rows, by the base surface 28. Each of the holes 32 is approximately ⅛ of an inch in diameter and is surrounded by a smooth depression in the base surface 28. Both of the groups of ventilation holes 32 are positioned between the convex medial edges 30 of the raised portions 29 and are spaced from each other across on the top and bottom of the lumbar support panel, on opposite sides of the narrowest distance between the convex medial edges. Such an arrangement of holes allows for ventilation and air circulation via the movement of moisture out of some holes and air into other, adjacent holes. It should be noted however, that the size, number and shape of the ventilation holes could be varied from the illustrated embodiment to suit the needs and activities of the wearer. For instance, more ventilation holes might be employed for athletic activities where the wearer is more likely to suffer from heavy perspiration.

The lumbar support panel 11 is preferably constructed of a relatively soft conforming material or materials that are breathable and generally "skin friendly," such as by having moisture wicking properties and smooth, soft and non-abrasive surfaces. Typically, these materials will include one or more of cotton, polyester or nylon. Preferably, the skin-adjacent surface of the support panel 11 is covered with a 100% textured polyester having an interlock stitch, an average yield of about 5¾ ounces per linear yard, a widthwise elongation of 100%, a length-wise elongation of 20% and an average width/length dimensional change of −2.5 and −2.33. Laminated, or otherwise attached to the skin-adjacent surface material is a foam backing preferably constructed of G45L polyether polyurethane foam having a density of 3.00+/−10% lbs/ft$^3$, a tensile strength of 25 psi (minimum) to 40 psi (average), an elongation of 90-125%, and a deflection @25% 105 lbs/50 in$^2$ (minimum) to 140 lbs/50 in$^2$ (average). Other types of foam material may be used as well, such as EVA, polyester, etc. and generally should fall within a density range of 2 to 5+/−10% lbs/ft$^3$.

The lumbar support panel 11 is preferably formed by placing the skin-adjacent material in a mold having the skin-adjacent surface shaped cavities defined therein, such as cavities defining the raised portions 29, with an adhesive on its inner surface. An expanded foam backing sheet is placed above the mold and is compressed with a flat compression plate, and optionally the addition of heat, to attach the foam backing to the skin-adjacent surface material and fill the mold cavities. Optionally, the materials can be laminated as a separate process prior to the forming process. Advantageously, the density of the raised portions 29 is generally lower, for a softer padding effect, than the more highly compressed base surface 28 which is somewhat stiffer to provide additional support and a firm attachment of the stitching lines connecting the panel to the strapping system, as described above. After attachment of the straps 12, 13 to the panel 11, the peripheral edge of the brace is trimmed in a single, long piece of banding material 33 for a finished look and to protect the edges of the material panels and the various stitch lines.

Figure 7:
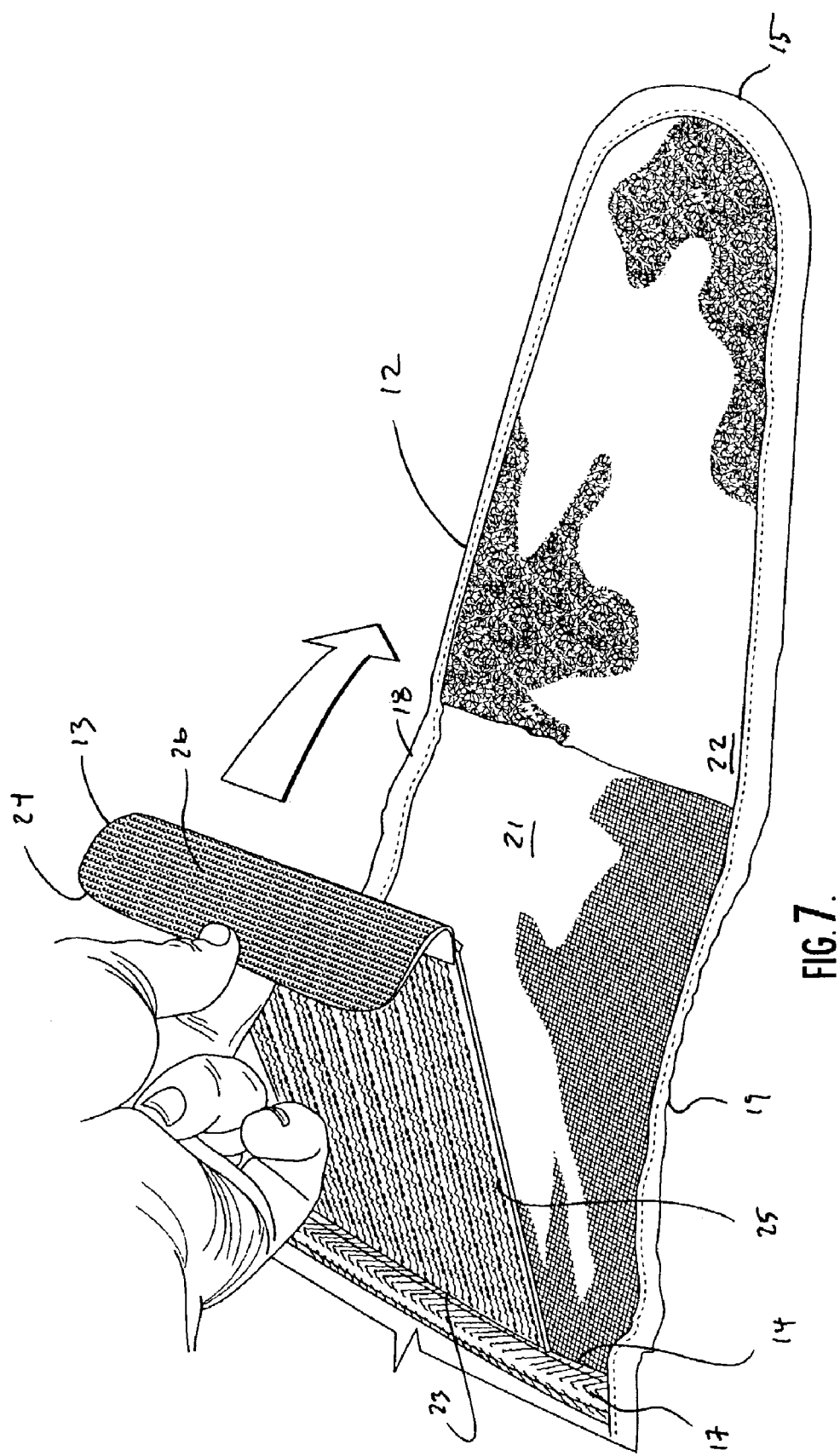
FIG. 7 is an enlarged perspective view of part of a strapping system of the back brace of FIG. 1, including a demonstration showing attachment of the outer straps to the main straps shown in FIG. 5.

During use, the wearer grips the main straps 12 of the back brace 10 and encircles his (or her) waist. The free ends 15 of the main straps are brought forward, and slightly upwards, over the wearer's hips and are secured together by attaching the hook material panel 34 on the inner surface of one of the free ends to the loop material on the outer surface of the other one of the free ends. While encircling the waist, or after attachment of the free ends 15 of the main straps 12, the wearer positions the lumbar support panel 11. The lumbar support panel 11 is positioned over the lower back region so that the convexly curved medial edges 30 of the pair of raised surface portions 29 are positioned on opposite sides of the wearer's spine. Tension is applied to the straps during overlapping attachment of the main straps 12, and additional tension is adjusted or supplied by adjustment of the amount of stretch in the elastic panel 25 of each of the outer straps 13. In particular, as shown in FIG. 7, the hook material panel 26 is removed from the loop material of the outer surface of the laminated panel 22 of the main strap and further stretched and reattached, resulting in the configuration shown in FIG. 3. Application and adjustment of the tension using the strapping system controls the amount of pressure applied to the lower back musculature by the lumbar support panel 11, and in particular the raised surface portions 29 on the erector spinae musculature. The pressure can then be varied to adjust the stability and comfort of the back brace, or just to allow evaporation of perspiration.

Among other advantages, the lumbar support panel 11 provides comfortable support for the wearer's lower back, in particular through the curved, convex shape of the raised portions 29 on its inner surface that fit the wearer's lordotic curve and avoid forming pressure points on the lower back musculature, especially along their medial edges 30. Further, the spacing between the raised portions 29 provides clearance for the spinous processes allowing support to be applied to the back musculature. The main and outer straps 12, 13 allow for adjustment of the tension in the back brace 10 and the amount of support provided by the panel 11. Overall, the strapping system is constructed of relatively thin, breathable and/or moisture wicking fabrics that are comfortable to wear even under clothing, immediately adjacent to the skin. Breathability is further increased by the materials selected for the support panel 11 and the ventilation holes 32 extending through the panel. The angle of the lateral edges 16 of the lumbar support panel 11 angle the main straps 12 upwards to extend comfortably over the hips of the wearer while maintaining the position of the support panel.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. For instance, a moisture wicking chemical could be applied to the inner surface of the lumbar support panel 11 to remove perspiration. Although specific terms are employed herein, they are used in a generic and descriptive sense only and not for purposes of limitation.

That which is claimed:

1. A back brace for supporting a lower back region of a wearer, including erector spinae musculature associated with a lower spine of the wearer, said back brace comprising:

a strapping system extending at least partially around a waist of the wearer; and a lumbar support panel connected to the strapping system and supported by the strapping system at the lower back region of the wearer, said lumbar support panel having an interior surface adjacent to the wearer's back defining a pair of raised portions wherein each of the raised portions is defined, in plan view, by a convexly curved medial edge having opposed ends, the opposed ends having a straight lateral edge extending therebetween and connecting the opposed ends, such that the convexly curved medial edge and the straight lateral edge cooperate to substantially define a semi-circular shape, wherein the convexly curved medial edges are configured to oppose each other, and to be positioned adjacent to and on opposite sides of the wearer's lower spine and to be spaced apart so as to contact the wearer's erector spinae musculature, wherein each of the raised portions extends outwardly from the lumbar support panel so as to form a smoothly curving convex surface configured to conform to the lordotic curve of the wearer's lower spine.

2. A back brace of claim 1, wherein the strapping system includes a pair of main straps each having a free end, at least one of the free ends having a connector disposed thereon, said connector configured to connect the free ends together so as to secure the main straps around the waist of the wearer.

3. A back brace of claim 2, wherein each of the main straps additionally includes a fixed end wherein the fixed ends are attached to the lumbar support panel.

4. A back brace of claim 3, wherein the main straps are portions of a single piece of material extending along an outer surface of the lumbar support panel.

5. A back brace of claim 3, wherein the strapping system further includes a pair of outer straps each extending over an outside surface of a respective one of the main straps wherein each of the outer straps includes a free end with a connector disposed thereon configured to attach to the outside surface of the respective one of the main straps.

6. A back brace of claim 5, wherein the connectors are hook and loop material connectors.

7. A back brace of claim 3, wherein the lumbar support panel further includes a pair of lateral edges to which the fixed ends of the main straps are attached.

8. A back brace of claim 7, wherein the lateral edges of the lumbar support panel are angled inwards at a top end and wherein the main straps extend therefrom at an upwards angle over the wearer's hips.

9. A back brace of claim 1, wherein the inner surface includes a base surface from which the raised portions extend outwards, said base surface extending at least between the convexly curved medial edges.

10. A back brace of claim 9, wherein a plurity of air holes are defined by the base surface and extended through the lumbar support panel.

11. A back brace of claim 10, wherein the air holes are positioned between the convexly curved medial edges of the raised portions.

12. A back brace of claim 11, wherein the air holes include two groups, one group positioned above a shortest distance between the convexly curved medial edges and the other group positioned below the shortest distance.

13. A lumbar support panel for supporting a lower back region of a wearer, including erector spinae musculature associated with a lower spine of the wearer, when applied against the lower back region with an associated strapping garment, said lumbar support panel comprising:
a base surface bounded by a peripheral edge;
said base surface having an interior surface adapted to be positioned adjacent to the wearer's back and having a pair of raised portions extending from the base surface wherein each of the raised portions is defined, in plan view, by a convexly curved medial edge having opposed ends, the opposed ends having a straight lateral edge extending therebetween, and connecting the opposed ends such that the convexly curved medial edge and the straight lateral edge cooperate to substantially define a semi-circular shape, wherein the convexly curved medial edges are configured to oppose each other, and to be positioned adjacent to and on opposite sides of the wearer's lower spine and to be spaced apart so as to contact the wearer's erector spinae musculature, wherein each of the raised portions extends outwardly from the lumbar support panel so as to form a smoothly curving convex surface configured to conform to the lordotic curve of the wearer's lower spine.

14. A lumbar support panel of claim 13, wherein the peripheral edge includes a pair of lateral portions spaced apart from each other and angled towards each other at an upper end.

15. A lumbar support panel of claim 14, wherein the peripheral edge includes a top and bottom portions spaced apart from each other and extending between upper and lower ends, respectively, of the lateral portions.

16. A lumbar support panel of claim 13, wherein the base surface extends at least between the convexly curved medial edges.

17. A lumbar support panel of claim 13, wherein the base surface extends between the raised portions.

18. A lumbar support panel of claim 17, wherein a plurality of air holes are defined by the base surface and extend through the lumbar support panel.

19. A lumbar support panel of claim 18, wherein the air holes are positioned between the convexly curved medial edges of the raised portions.

20. A lumbar support panel of claim 19, wherein the air holes include two groups, one group positioned above a shortest distance between the convexly curved medial edges and the other group positioned below the shortest distance.

21. A lumbar support panel of claim 20, wherein the base surface and raised portions are constructed of a single piece of material.

22. A method of using a back brace to support a lower back region of a wearer, including erector spinae musculature associated with a lower spine of the wearer, said method comprising:
encircling the wearer's waist with a pair of main straps attached to a lumbar support panel;
positioning the lumbar support panel over the lower back region so that a pair of raised portions, wherein each of the raised portions is defined, in plan view, by a convexly curved medial edge having opposed ends, the opposed ends having a straight lateral edge connecting the opposed ends and extending therebetween, such that the convexly curved medial edge and the straight lateral edge cooperate to substantially define a semi-circular shape, wherein the convexly curved medial edges are configured to oppose each other, and to be positioned adjacent to and on opposite sides of the wearer's lower spine, and to be spaced apart so as to contact the wearer's erector spinae musculature, wherein each of the raised portions extends outwardly from the lumbar support panel so as to form a smoothly curving convex surface, and to conform to the lordotic curve of the wearer's lower spine; and
applying tension to the main straps and attaching free ends of the main straps to each other so as to apply and maintain compression on the erector spinae muscles and conform to the lordotic curve of the wearer's lower spine with the raised portions.

23. A method of claim 22, further comprising applying additional tension to the raised portions by applying tension to a pair of outer straps each extending over an outside surface of a respective one of the main straps and attaching the outer straps to the main straps.

24. A method of claim 22, wherein positioning the lumbar support panel includes positioning a pair of lateral edges of the panel so that top portions of the lateral edges are angled inwards and the main straps extend upwards and over the wearer's hips.

* * * * *

UNITED STATES PATENT AND TRADEMARK OFFICE
CERTIFICATE OF CORRECTION

PATENT NO. : 7,364,558 B2  Page 1 of 1
APPLICATION NO. : 10/274351
DATED : April 29, 2008
INVENTOR(S) : Weaver, II et al.

It is certified that error appears in the above-identified patent and that said Letters Patent is hereby corrected as shown below:

Column 9,

Line 29, "plurity" should read --plurality--;

Line 30, "extended" should read --extend--.

Signed and Sealed this

Fifteenth Day of July, 2008

JON W. DUDAS
*Director of the United States Patent and Trademark Office*